United States Patent [19]

Cardellina, II et al.

[11] Patent Number: 4,929,270

[45] Date of Patent: May 29, 1990

[54] METHOD OF INDUCING CHLOROSIS IN A KNAPWEED PLANT

[75] Inventors: John H. Cardellina, II, Bozeman; Andrea C. Stierle, Butte; Gary A. Strobel, Bozeman, all of Mont.

[73] Assignee: Research and Development Institute, Inc. at Montana State University, Bozeman, Mont.

[21] Appl. No.: 177,536

[22] Filed: Apr. 4, 1988

[51] Int. Cl.[5] .................. A01N 43/90; C07D 487/04; C07D 487/14; C07D 513/18

[52] U.S. Cl. .......................................... 71/92; 71/90; 544/5; 544/343; 544/349

[58] Field of Search ............................ 544/349; 71/92

[56] References Cited

U.S. PATENT DOCUMENTS

| | | | |
|---|---|---|---|
| 3,314,959 | 4/1967 | Hoffman | 544/349 |
| 3,422,110 | 1/1969 | Stadler | 544/349 |
| 4,609,657 | 9/1986 | Stadler | 544/349 |

OTHER PUBLICATIONS

Kamikawa, Chem Abs, 92,4211984m (1980).

*Primary Examiner*—Mark L. Berch
*Attorney, Agent, or Firm*—Lowe, Price, LeBlanc, Becker & Shur

[57] ABSTRACT

A method of selectively inducing chlorosis on a knapweed plant while sparing other plants comprises applying a knapweed phytotoxic amount of the L,L isomer of the cyclodipeptide of the invention to a field at a period in time prior, during or subsequent to the emergence of the plants; and allowing for the cyclodipeptide to remain in contact with the plants for a period of time effective to attain the phytotoxic effect.

8 Claims, No Drawings

METHOD OF INDUCING CHLOROSIS IN A KNAPWEED PLANT

TECHNICAL FIELD

This invention relates to spotted knapweed specific phytotoxin compounds isolated from the fungus of an infected plant collected in the wild and to the synthetically prepared compounds. This invention also relates to the utilization of the compounds for the biocontrol of spotted knapweed in cultivated areas.

BACKGROUND ART

Fungi have long been recognized as instigators of plant diseases associated with the elaboration of one or more phytotoxins. To date, phytotoxins having the unique property of expressing host specificity at the species or cultivar level are known only from pathogens of crop plants. This is probably due to the fact that agrosystems with a strictly homogeneous genetic base serve as a huge reservoir of essentially identical plant material. This homogeneity renders such species susceptible to widespread devastation by one or more pathogens.

The 1970 Southern corn leaf blight epidemic in the U.S.-Canada, attributed to the pathogenic fungus Dreschlera maydis, is a case in point (Tatum, L. A. (1971) Science 171, 1113–1115). Thus, a pathogen has the potential to develop and spread quickly under such conditions and can easily be observed and isolated. Common weedy plants, however, usually exist in a population having a broad, mixed genetic base which tends to preclude the development of such an epidemic, making discovery of the pathogen difficult, if not impossible.

The detection and study of weed pathogens is important not only for their intrinsic ability to serve as biocontrol agents, but also because of their propensity to produce novel bioactive substances. These substances could become novel herbicides or provide important chemical leads to the herbicide industry (Strobel, G. A., Sugawara, F. & Clardy, J. (1987), in Allelochemica: Role in Agriculture and Forestry, ed. Waller, G. R. (American Chemical Society, Washington, 516–523).

Spotted knapweed (Centaurea maculosa) now poses a significant threat as a weed species, having invaded rangelands of the northwestern United States and southwestern Canada. Since its introduction to the United States in the early 1900's, this hardy composite has occupied millions of acres with an estimated 70% decline in forage production (Harris, P. & Cranston, R. (1979) Can. J. Plant Sci. 59, 375–382). Its rapid spread has been aided by a lack of natural predators in North America and by an ability to compete successfully with native grasses (Myers, J. H. & Berube, D. E. (1983) Can. J. Plant Sci. 63, 981–987).

Diketopiperazines are in general known in the art (See for example Patent Publication No. DD-224216 (Dec. 30, 1981)). However, the diketopiperazines described in this reference are a general group of diketopiperazines utilized as substrates for the preparation of N-lysergic aminoacylactam derivatives. No phytotoxic activity is described in the reference for these compounds. The isolation and identification of a host specific toxin against an important weed pest has important biological implications.

Various form species of A. alternata have been credited with production of host specific phytotoxins for crop plants. To date, several such toxins have been isolated and identified from various pathotypes of this organism (Nishimura, S. & Kohmoto, K. (1983) Ann. Rev. Phytopathol. 21, 87–116).

Several host specific toxins isolated to date from Alternaria alternata include compounds that are active against important cultivars of a variety of crop plants such as pears, apples, citrus, and tomatoes (Itoh, M., Hagiwara, D. & Kamiya, T. (1975) Tetrahedron Letters 49, 4393–4394). The value of a highly specific toxin to economically desirable plants resides not only in its herbicidal potential but in its utility as a screening agent. Cultivars of a particular plant can be challenged by the toxin and resistant individuals can be disseminated (Strobel, G. A. (1982) Ann. Rev. Biochem. 51, 309–333).

However, the discovery of a weed specific toxin represents an even more compelling possibility as a direct biocontrol agent.

DISCLOSURE OF THE INVENTION

This invention relates to a cyclodipeptide of the formula

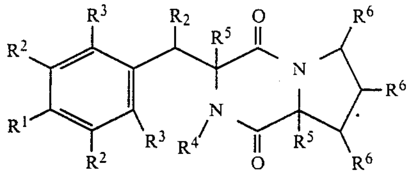

wherein $R^1$ is selected from the group consisting of R, OR, $NR_2$ and SR, wherein R is H or ($C_1$-$C_5$) alkyl, alkenyl, alkynyl,F, Cl, Br, I, $NO_2$ and $CF_3$;

each $R^2$ independently is selected from the group consisting of $R^1$, COOR and OOCR, wherein R is as defined above;

$R^4$ is R;

$R^3$ is $R^2$, or $R^3$ and $R^4$ together are a single bond or $CH_2$;

each $R^5$ independently is selected from the group consisting of R, OR and SR, or the two $R^5$ are C-C or S-S, wherein R is as defined above; and each $R^6$ independently is selected from the group consisting of $R^2$ and halogen.

This invention also relates to a method of selectively inducing phytotoxicity on a spotted knapweed plant, comprising applying a knapweed phytotoxic amount of the L,L isomer of the cyclodipeptide of this invention to the plant; and allowing for the cyclodipeptide to remain in contact with the plant for a period of time effective to attain said effect.

This invention also relates to a method of selectively inducing chlorosis on a spotted knapweed plant while sparing plants other than the knapweed, comprising applying a knapweed phytotoxic amount of the L,L isomer of the cyclodipeptide of this invention which is sparing of plants other than knapweed to a field at a period of time prior, during or subsequent to the emergence of said plants; and allowing for the cyclodipeptide to remain in contact with said plants for a period of time effective to attain said effect.

This invention also relates to a method of selectively reducing the growth of a spotted knapweed plant, comprising applying a knapweed growth reducing amount of the L,L isomer of the cyclodipeptide of this invention to the plant; and allowing for the cyclodipeptide to remain in contact with said plant for a period of time effective to attain said effect.

This invention also relates to a method for selectively reducing the growth of a spotted knapweed plant while sparing plants other than the knapweed, comprising applying a knapweed growth reducing amount of the L,L isomer of the cyclodipeptide of the invention to a field prior, during or subsequent to the emergence of said plants; and allowing for said cyclodipeptide to remain in contact with said plants for a period of time effective to attain said effect.

This invention also relates to a knapweed specific phytotoxic composition obtained by a method comprising growing as knapweed phytotoxic fungus in a culture medium for a period of time and under conditions effective for the fungus to exude phytotoxins into said medium;

separating said phytotoxin-containing medium from the fungus; and separating out from said medium a fraction thereof comprising compounds of a molecular weight greater than about 1200 to obtain said knapweed specific phytotoxic composition.

A more complete appreciation of the invention and many of the attendant advantages thereof will be readily perceived as the same becomes better understood by reference to the following detailed description of the preferred embodiments thereof.

BEST MODE FOR CARRYING OUT THE INVENTION

This invention arose from a biorational approach to control the tenacious spotted knapweed consisting of locating a host specific or selective pathogen of spotted knapweed and employing either the pathogen or its phytotoxic metabolites as control agents. The initial work conducted on this invention was done with an infected plant of the black leaf blighted Centaurea maculosa.

The exemplary causal organism was identified as Alternaria alternata. This organism was grown in liquid culture in accordance with the invention and shown to produce a number of phytotoxins (Stierle, A. C., Cardellina, J. H., II & Strobel, G. A. (1987) J. Nat. Prod., submitted for publication, the entire content of which is incorporated herein by reference).

This invention provides a group of diketopiperazines comprising the above described phytotoxins and analogs thereof. Among the knapweed selective phytotoxins identified are maculosin or cyclo(L-Pro-L-Tyr) and cyclo(L-Pro-L-Phe). These are to the inventors' knowledge the first example of host-specific toxins to be synthesized or isolated from a weed pathogen.

*Centaurea maculosa* is considered by farmers and ranchers in the northwestern states as their primary weed problem. Grazing animals avoid knapweed. It is thought to produce allelochemicals which seem to facilitate its rapid spread through rangeland.

Nearly two months of intense searching through several counties in southwestern Montana and an examination of about twelve hundred plants culminated in the discovery of a seriously compromised plant on the northern slope of Big Butte, a five hundred foot cinder cone in Butte, Montana. Approximately thirty percent of the aerial leaves and ninety percent of the flowers of the plant were covered by either black fungal growth or dark brown, weeping lesions.

The phytotoxins, e.g., maculosin and cyclo(L-Pro-L-Phe) are isolated by growing the fungus, e.g., Alternaria fungus, in a culture medium to allow the production of phytotoxic compounds which are exuded into the medium. The mycelia are filtered out, e.g., with filter paper, and the medium kept. The medium is then extracted with a solvent which is moderately polar and non-water soluble, e.g., ethyl acetate or methylene chloride, mixtures thereof and the like). Other solvents may also be utilized but preferred are organic solvents which are moderately polar. The extract may then be evaporated to dryness to obtain a powder which is not host specific although phytotoxic. This powder contains, in addition to the present phytotoxins, e.g., tenuazonic acid and other toxins which are not knapweed specific.

The separation of the present phytotoxin compounds may then be conducted by size exclusion, e.g., with a Sephadex LH-20 column which has a cutoff molecular weight of less than about 1200. The thus obtained product is a mixture of the two phytotoxins of the invention and is host specific. Thus, when this composition is applied to, e.g., johnsongrass, it does not have a phytotoxic effect on it. Further purification can be obtained by size exclusion or gel permeation chromatography with some partition effect, e.g., with Bio-beads made of polystyrene such as SX8 beads. The aromatic rings of the phytotoxins of the invention respond to this type of chromatography by separating the H and OH substituted compounds. Separate fractions are obtained, e.g., with the maculosin emerging first.

The compositions resulting from the size exclusion separation steps may be used as they are or may be dried, e.g., by evaporation. The products may then be recrystallized from a solvent such as methanol or methylene chloride or mixtures thereof or mixtures thereof with water. Other solvents may also be utilized as is known in the art. The two phytotoxins can be obtained by the above method with a purity greater than about 95%.

An alternative method for the steps subsequent to the size exclusion step where all molecules having a molecular weight greater than about 1200 are eliminated, comprises subjecting the remaining medium to centrifugal counter current chromatography and monitoring the appearance of discrete fractions by means of, e.g., an ultraviolet monitor (CRC Critical Reviews in Analyt. Chem. 17(1):65–143, Itoh Ioshiro (1986)).

As in the previous case the composition may be used as is or the medium may be evaporated and the compounds recrystallized from solvents such as those described above. The purity of the two compounds obtained in this manner can also be greater than about 95% as determined by gas chromatography-mass spectrometry.

The compounds of this invention may also be synthesized by methods known in the art (see, Itoh, M., Hagiwara, D. & Kamiya, T. (1975) Tetrahedron Letters 49, 4393–4394; and Nitecki, D.., Halpern, B. & Westley, J. W. (1967) J. Org. Chem. 33, 864–866, the entire contents of which are incorporated herein by reference).

The compounds of the invention have been found to be selectively phytotoxic for knapweed while sparing other plants to which they are applied. In the particular case of maculosin it shows phytoxicity for knapweed while sparing a variety of dicot plants such as lettuce, lemon, tomato, apple, sunflower, cucumber, leafy spurge, marigold, dandelion, sagebrush, thistle and crown of thorns, among others, and monocot plants such as johnsongrass, annual bluegrass, park oat, quack grass, crab grass and corn, among others.

In addition, both maculosin and cyclo(L-Pro-L-Phe) have been shown not to be toxic against bacteria, both gram positive and negative bacteria such as *Bacillus subtilis, S. aureus, E. coli, Corynebacterium michiganensis, Xanthomonas campestris,* and *Pseudomonas aeruginosa,* among others, yeast such as *Candida albicans* which is a human pathogen, and the like. In addition, the phytotoxins have also been shown not to be cytotoxic as measured by the brine shrimp test. In accordance with this test 25 to 30 live brine shrimp larvae are placed in about 4 ml of instant ocean water or saline. One mg of the pure phytotoxin is then mixed into the medium and 24 to 48 hours allowed to elapse while the number of live brine shrimp is observed. In various tests conducted with the phytotoxins of the invention not one brine shrimp larva was observed to die.

The phytotoxic compounds of the invention can impair the ability of knapweed to grow. For instance, when a site on the plant is nicked and the compounds are applied to the nicked area, necrosis can be observed after a few hours. The compounds of the invention are in general slow acting and at times it is necessary to wait for up to about 72 hours or more to observe the effects. In general the phytotoxic effect results in that the plants may rot or suffer from necrosis or chlorosis, all of which impair their growth.

Chlorosis appears in a plant by substantial loss of its chlorophyll. When the compounds of this invention are applied to a knapweed plant or to the area where the plant grows without nicking or damaging a portion thereof, in general chlorosis ensues. Spraying of a solution containing the compounds will also often result in chlorosis. Moreover, the plant may be killed subsequent to an initial impairment of flowering and prevention from producing and dropping seeds. This is of particular importance because it impairs the capability of the plants to reappear the next season by means of new seedlings or hypocotyl. The killing effect can be observed when the compounds of the invention are applied at higher concentrations or by repeated dosage of the plants.

The phytotoxic compounds of the invention have the formula

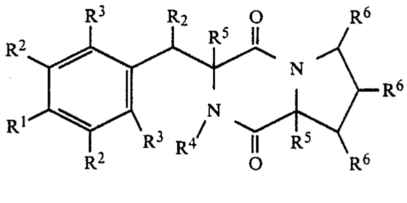

wherein $R^1$ is selected from the group consisting of R, OR, $NR_2$ and SR, wherein R is H or ($C_1$-$C_5$) alkyl, alkenyl, alkynyl F, Cl, Br, I, $NO_2$ and $CF_3$;

each $R^2$ independently is selected from the group consisting of $R^1$, COOR and OOCR, wherein R is as defined above;

$R^4$ is R;

$R^3$ is $R^2$, or $R^3$ and $R^4$ together are a single bond or $CH_2$;

each $R^5$ independently is selected from the group consisting of R, OR and SR, or the two $R^5$ are C—C or S—S, wherein R is as defined above; and each $R^6$ independently is selected from the group consisting of $R^2$ and halogen.

Preferred among the cyclodipeptides of the invention are those wherein $R^1$ is OH and $R^2$–$R^6$ are H. Another preferred group is that wherein $R^1$ is H and $R^2$–$R^6$ are H. Another preferred group encompasses the compounds wherein $R^1$ is OH or H and $R^2$–$R^6$ are other than H. Still another preferred embodiment of the invention is that wherein the cyclodipeptides of the invention are in substantially pure form. The cyclodipeptides wherein $R^1$ is H or OH and $R^2$–$R^6$ are H can be obtained by direct synthesis or from a culture of Alternata by the method described above and exemplified below. The remaining compounds may be prepared via a synthetic route in accordance with Itoh, M., Hagiwara, D. & Kamiya, T. and Nitecki, D. E., Halpern, B. & Westley, J. W., supra.

The compounds may be further purified by extraction and recrystallization, both methods known in the art.

This invention also provides a phytotoxic composition comprising the cyclodipeptide of the invention and a carrier. The carrier may be a liquid or a solid carrier. The liquid carrier may be an organic solvent or mixtures thereof or mixtures thereof with water, in amounts which may dissolve the compound. The solid carrier may be any solid carrier known in the art, e.g., diatomaceous earth. Organic solvents which may be utilized as liquid carriers are ethanol, methanol, and dimethyldisulfoxide, among others. However, any carrier which is not toxic to plants other than knapweed, which may be growing in the area to be treated, can also be used.

The compounds and the composition of the invention may be applied directly to the leaves, with or without nicking, to the area surrounding the plant or to the entire plant. In general, one application will suffice although the compounds and compositions are slow acting and it may take up to about 72 hours or more for the first effects to appear. Repeated applications of the phytotoxic compounds of the invention may be undertaken as desired, particularly in situations where it is suspected that perhaps a heavy rain may have eliminated at least part of the compounds applied to the plants.

In a preferred embodiment of the phytotoxic composition described above, the cyclodipeptide is present in an amount of about 0.01 to 99.99 wt % of the composition, and more preferably 0.1 to 50 wt % of the composition. Still more preferred is a composition wherein the cyclodipeptide is present in an amount of about 1 to 50 wt %, and still more preferred about 10 to 20 wt % of the composition. When the carrier is a liquid capable of dissolving the dipeptide, the composition may be provided as an at least about 10-5M cyclodipeptide solution of the dicyclopeptide in the carrier.

In general, the compounds of the invention may be applied in an amount of about 0.00001 to 1 mole/plant, more preferably about 0.0001 to 0.5 mole/plant. Repeated applications may also be conducted.

Also provided herein is a method of selectively inducing phytotoxicity on a knapweed plant which comprises applying a knapweed phytotoxic amount of the cyclodipeptide of the invention to the plant or the area around it and allowing for the cyclodipeptide to remain in contact with the plant for a period of time effective to induce phytotoxicity on the plant.

In a preferred embodiment of the method of selectively inducing phytotoxicity on the knapweed plant, prior to applying the compound the plant is nicked and the cyclodipeptide is then applied to the nicked area to induce the phytotoxicity. Often when the cyclodipeptide of the invention is applied in this manner the phytotoxicity is evidenced by necrosis of the area around the nicked area or general chlorosis of the plant where decoloration is perceived.

In cases where the cyclodipeptide is applied in general to the plant without nicking portions thereof the phytotoxicity takes the form of chlorosis.

In the field, instead of manually nicking the plants they can be crushed, furrowed or thrashed either by hand or by mechanical means.

In one particularly preferred embodiment of the method described above the cyclodipeptide is applied to a field at a time prior to the emergence of the knapweed plant. When applied in this manner the phytotoxic cyclodipeptides become in contact with the emerging seedlings at an early time and are better equipped to produce damage to the knapweed plant.

This invention also provides a method of selectively inducing phytotoxicity on a knapweed plant while sparing plants other than knapweed which comprises applying a knapweed phytotoxic amount of the cyclodipeptide of this invention to a field at a period in time prior, during or subsequent to the emergence of the plants, said amount being sparing of other plants, and allowing for the cyclodipeptide to remain in contact with the plants for a period of time effective to selectively induce phytotoxicity on the knapweed while sparing the remaining plants.

Preferred conditions for the practice of this method are those where the phytotoxic cyclodipeptide is applied directly to the knapweed with or without previous crushing of the plants. When other plants are growing in the same field as the knapweed this pretreatment may not be feasible. In such cases direct application of the phytotoxic cyclodipeptides to the field by means such as spraying may be appropriate.

Also provided by this invention is a method of selectively reducing the growth of a knapweed plant which comprises applying a knapweed growth reducing amount of the cyclodipeptide of the invention to the plant, and allowing for the cyclodipeptide to remain in contact with the plant for a period of time effective to evidence a reduction in the growth of the plant.

Also provided herein is a method for selectively reducing the growth of a knapweed plant while sparing plants other than knapweed which comprises applying a knapweed growth reducing amount of the cyclodipeptide of the invention to a field prior, during or subsequent to the emergence of said plants, and allowing for said cyclodipeptide to remain in contact with said plants for a period of time effective to reduce the growth of the knapweed while sparing the remaining plants growing in the field.

Preferred embodiments of these methods comprise conditions described in the prior methods, e.g., applying the cyclodipeptide as an at least about $10^{-5}$ M solution in a liquid carrier. Also a preferred embodiment is that wherein the method further comprises nicking the knapweed plant prior to applying the cyclodipeptide to the nicked area.

Other preferred conditions for the practice of the above methods are described hereinabove.

Also part of the invention are knapweed specific or selective phytotoxic compositions obtained by a method which comprises growing a knapweed phytotoxic fungus such as Alternata in a culture medium for a period of time and under conditions effective for the fungus to exude phytotoxins into the medium and separating the phytotoxins-containing medium from the fungus mycelia, e.g., by filtering the medium. This composition contains various phytotoxins which are not specific for knapweed along with the knapweed-specific phytotoxins of the invention. The composition is further processed by separating out from the medium a fraction thereof comprising compounds of a molecular weight greater than about 1200 to obtain the knapweed specific phytotoxic composition. The composition may be utilized as is, or the medium may be separated from the remaining compounds, e.g., by evaporation, and a composition of a desired content of cyclodipeptides prepared for utilization in the containment of knapweed in accordance to this invention.

A preferred embodiment of the above knapweed specific phytotoxic composition is that obtained by the method described above further comprising subjecting the composition to affinity chromatography to separate first and second fractions, the first fraction comprising cyclo(L-Pro-L-Tyr) and the second fraction comprising cyclo(L-Pro-L-Phe).

Having now generally described this invention, the same will be better understood by reference to certain specific examples, which are included herein for purposes of illustration only and are not intended to be limiting of the invention or any embodiment thereof unless so specified.

EXAMPLES

The causal organism, *Alternaria alternata* is grown in liquid culture and shown to produce a number of phytotoxins among which are maculosin and cyclo(L-Pro-L-Phe) (Stierle, A. C., Cardellina, J. H., II & Strobel, G. A. (1987) J. Nat. Prod., submitted for publication, the entire content of which is incorporated herein by reference). These are the first examples of host-specific toxins isolated from a weed pathogen.

Fungal Pathogenicity

Identification of a fungal pathogen requires both isolation of pure cultures of fungi and determination of disease inductive ability of fungal isolates.

Fungi are established as pure cultures by repeated single spore transfers followed by morphological examination.

Pathogenicity is determined by challenging healthy knapweed plants with pure fungal cultures. Healthy plants are nicked in various locations on their leaves and stems. Pieces of mycological agar are impregnated with the test fungus and applied to 50% of these sites. Sterile plastic bags are placed over 10 plants to heighten humidity, and 5 plants are left open to the air. Plants are grown under controlled conditions of 12 hr of light and 12 hr of darkness at 25° C. and examined daily for initiation of mycelial growth and induction of disease symptoms. It is apparent that elevated humidity is essential for promotion of growth of the fungal mycelia within the plant. In no case are untreated sterile nicks sites of infection.

Fungal Culture

*Alternaria alternata* is maintained on DIFCO mycological agar plates containing a 2% knapweed effusion (vol/vol) to insure solicitation of toxicity. The fungus is cultivated for toxin production in 1 liter still cultures of modified Czapek-Dox medium also containing 2% knapweed effusion (vol/vol). Crude extracts of the fungus grown without the effusion are less toxic than those grown with it. The effusion itself exhibits no toxicity when applied directly to any of the test plants. Plants used in this study are grown under controlled environmental conditions of 12 hr of darkness and 12 hr of light ($4.4 \times 10^4$ lux) at 25° C.

Leaf Assay

A simple leaf-puncture assay is used as a guide in isolating potential phytotoxins (Sugawara, F., Strobel, G. A., Fisher, L. D., Van Duyne, G. D. & Clardy, J. (1985) Proc. Natl. Acad. Sci. USA 82, 8291–8294, the entire content of which is incorporated herein by reference). The test fraction is dissolved in 2% ethanol and applied to the nicked surface of the host leaf in a 5 äl droplet. The leaf is sealed in a Petri dish containing moistened filter paper and incubated for 72 hours. The symptoms that develop vary from no reaction to the formation of a weeping necrotic lesion that engulfs the entire leaf blade.

Crude extracts are tested at 1000 ppm, column fractions are tested at 100 ppm, and pure compounds are tested at $10^{-3}$, $10^{-4}$, and $10^{-5}$ M. All tests are conducted on 15–20 leaves per assay. Leaves of both spotted knapweed and johnsongrass (*Sorghum halapense*) are used.

Hypocotyl Assay

An assay that involves nicking the hypocotyl of appropriate host seedlings and applying the test fraction in a 2% ethanol solution in a manner similar to the leaf assay is also employed. Symptoms usually develop within 48 hours and range from no reaction to total necrosis of the plant material. In no circumstances are deleterious symptoms induced by application of 2% ethanol solution in either the leaf or hypocotyl assays.

Mass Culture and Extraction

*Alternaria alternata* is grown in five liter batches of broth culture which are harvested after a 24 day incubation period of 25° C. Suction filtration is used to separate the mycelial mat from the liquid medium. The filtrate is sequentially, exhaustively extracted with four 500 ml portions of $CH_2Cl_2$, which is then extracted with four 500 ml aliquots of ethyl acetate (EtOAc), which are also combined and evaporated to give an oily residue (0.675 g). The aqueous fraction is freeze-dried and along with the two organic fractions, tested for phytotoxicity against knapweed at a concentration of 1000 ppm.

Both organic fractions induce the formation of large necrotic lesions in 48 hours, but the aqueous fraction causes no apparent tissue damage, even after 96 hours. The fungal mat is extracted in a similar manner after pulverization in a Waring blender, but none of the extracts produce lesions on knapweed leaves.

EXAMPLE 1

Test of Pathogenicity and Fungal Identification

A compromised *Centaura maculosa* or knapweed plant is collected and returned to the laboratory where several pieces of tissue are carefully excised and placed on DIFCO bacto-agar. Three morphologically distinct fungi are apparent after a 48 hr incubation period. These are separated and placed on DIFCO mycological agar plates containing 2% knapweed effusion. The fungi are first established as pure cultures before their role in knapweed toxicity is assessed.

Following the mandate of Koch's postulates, the nature of the pathogen is determined by challenging healthy knapweed plants with pure isolates of the fungi applied to nicked sites on the plants. Only one of the fungal isolates induces the formation of weeping necrotic lesions within a 5 day period. The apparent pathogen is reisolated from the disease-induced plants and is morphologically identical to the applied fungus. The organism is identified as *Alternaria alternata Lam* by the CBS Mycological Laboratory in Baarn, Netherlands. Mass culture of the isolate is initiated to determine whether this propensity for phytotoxin production can be exploited against spotted knapweed.

EXAMPLE 2

Isolation and Identification of Diketopiperazines

The ethyl acetate soluble extracts of the culture filtrate are permeated through Bio-Beads S-X4 (hexane-$CH_2Cl_2$-EtOAc, 4:3:1, v/v). The fourth, fifth and sixth of twelve fractions obtained are phytotoxic. Size exclusion chromatography of fraction five on Sephadex LH-20 ($CH_2Cl_2$-MeOtBu-iPrOH, 1:1:1, v/v) yields maculosin (1) (see Scheme).

SCHEME

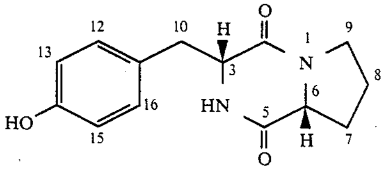

1

-continued

SCHEME

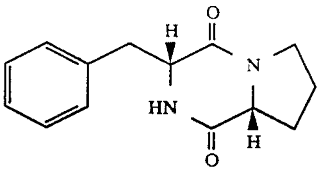

2

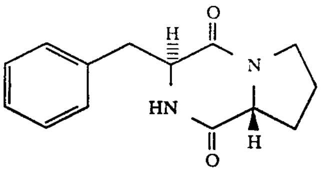

3

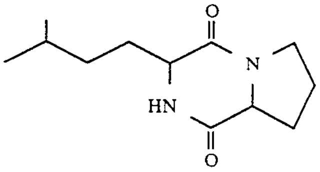

4

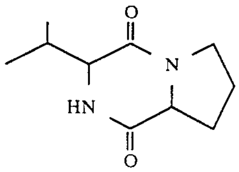

5

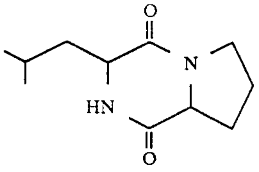

6

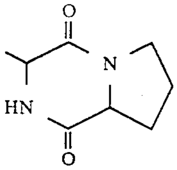

7

Similar treatment of fraction six gives a mixture which can only be resolved by centrifugal countercurrent chromatography ($CHCl_3$-MeOH-$H_2O$, 25:34:20, v/v, lower phase mobile) to (2) and (3) (See Scheme above). Fraction four provides diketopiperazine (4) (see Scheme above) upon further size exclusion chromatography on Bio-Beads S-X8 ($CH_2Cl_2$-cyclohexane, 3:2, v/v).

The dichloromethane soluble extracts are permeated through Sephadex LH-20 with $CH_2Cl_2$-MeOH (1:1, V/V). The one active fraction yields compounds (5), (6) and (7) when subjected to centrifugal countercurrent chromatography as described above (See Scheme). Compounds (1) and (2) are found to be phytotoxic to spotted knapweed.

Table 1 herebelow summarizes the isolation data for the diketopiperazines (1)-(7) (See Scheme).

TABLE 1

Summary of Isolation Data, Diketopiperazines 1-7

| Compound | Molecular Weight/ Formula | Isolation Method[a] | Rt[b] | % Yield[c] |
|---|---|---|---|---|
| 1 | 260/$C_{14}H_{16}N_2O_3$ | Sephadex LH-20[d] | 2.10 | 0.74 |
| 2 | 244/$C_{14}H_{16}N_2O_2$ | CCC[e] | 0.38 | 0.39 |
| 3 | 244/$C_{14}H_{16}N_2O_2$ | CCC[e] | 0.45 | 0.44 |
| 4 | 224/$C_{12}H_{20}N_2O_2$ | Bio-Beads S-X8[f] | 1.33 | 0.23 |
| 5 | 196/$C_{10}H_{16}N_2O_2$ | CCC[e] | 0.70 | 0.10 |
| 6 | 210/$C_{11}H_{18}N_2O_2$ | CCC[e] | 0.63 | 0.23 |
| 7 | 168/$C_8H_{12}N_2O_2$ | CCC[e] | 0.56 | 0.08 |

[a]Final step in purification
[b]Retention time in hours
[c]% yield = mass of compound obtained/mass of total organic extract × 100
[d]Column 2 × 135 cm; eluant $CH_2Cl_2$—MeOtBu—iPrOH (1:1:1, v/v); flow rate 1.9 mL/min
[e]Column volume 285 mL; eluant $CHCl_3$—MeOH—$H_2O$ (25:34:20, v/v); flow rate 4 mL/min; lower phase mobile
[f]Column 2.5 × 140 cm; eluant $CH_2Cl_2$-cyclohexane (3:2, v/v); flow rate 1.5 mL/min The molecular formula of (2) is determined to be $C_{14}H_{16}N_2O_3$ by high resolution mass spectrometry. Phenolic and amide functional groups are indicated by infrared absorptions at 33480 and 1670 $cm^{-1}$, respectively.

Detailed analyses of the mass spectral fragmentation and $^1H$-NMR data results in the proposal of structure (1) (See Scheme above). The absolute stereochemistry is established by the synthesis of cyclo(L-Pro-L-Tyr) from the t-BOC derivative of L-proline (Itoh, M., Hagiwara, D. & Kamiya, T. (1975) Tetrahedron Letters 49, 4393–4394, the entire content of which is incorporated herein by reference) and the methylester of L-tyrosine following known procedures. This approach is known to proceed without racemization (Nitecki, D. E., Halpern, B. & Westley, J. W. (1967) J. Org. Chem. 33, 864–866, the entire content of which is incorporated herein by reference).

The synthetic and natural materials are shown to be identical by $^1H$-NMR, mass spectrometry, optical rotation and phytotoxicity. $^1H$-NMR mass spectrometry reveals that compounds (2) and (3) (See Scheme above) are stereoisomers of composition $C_{14}H_{16}N_2O_2$.

Infrared spectroscopy indicates an amide moiety, and $^1H$-NMR decoupling provides the gross structure cyclo-Pro-Phe. Comparison of the $^1H$-NMR spectra and optical rotation with those of synthetic materials identifies compound (2) as cyclo(L-Pro-L-Phe) and compound (3) as cyclo(L-Pro-D-Phe) (Young, P. E., Madison, V. & Blout, E. (1975) J. Am. Chem. Soc. 98, 5365–5371, the entire contents of which is incorporated herein by reference).

The remaining four diketopiperazines, (4)-(7) (See Scheme above), are identified in the same manner. The molecular formulae are determined by mass spectrometry, the structural details are worked out from IR and mass spectral fragmentations and $^1H$-NMR decoupling experiments.

EXAMPLE 3

Biological Activity

Once the seven diketopiperazines are isolated and identified, they are examined for phytotoxicity. The compounds are first applied to knapweed leaves and hypocotyls following the protocol outlined above. The most active isolate is compound (1) (See Scheme above), cyclo(L-Pro-L-Tyr), which exhibits lesion inductive abilities at $10^{-3}$, $10^{-4}$ and $10^{-5}$ M At $10^{-6}$ M a slight necrotic fleck appears in 72 hours but that is not considered active by the standards established (see Table 2 herebelow).

TABLE 2

Summary, Host Specificity Screening of Maculosin

| | Maculosin (1): | | | | | |
|---|---|---|---|---|---|---|
| | Natural | | | Synthetic | | |
| CONCENTRATION (M) | $10^{-3}$ | $10^{-4}$ | $10^{-5}$ | $10^{-3}$ | $10^{-4}$ | $10^{-5}$ |
| DICOTS | | | | | | |
| *Centaurea maculosa* (knapweed) | +++ | ++ | + | +++ | ++ | + |
| *Lactuca sativa* L. (lettuce) | − | − | − | − | − | − |
| *Citrus limon* L. (lemon) | − | − | − | − | − | − |
| *Lycopersicon esculentum* Mill. (tomato) | − | − | − | − | − | − |
| *Malus sylvestris* Mill. (apple) | − | − | − | − | − | − |
| *Helianthus anuus* L. (sunflower) | − | − | − | − | − | − |
| *Cucumis sativis* L. (cucumber) | − | − | − | − | − | − |
| *Euphorbia esula* L. (leafy spurge) | − | − | − | − | − | − |
| *Bidens pilosa* L. (bur marigold) | − | − | − | − | − | − |
| *Taraxacum officinale* Weber (dandelion) | − | − | − | − | − | − |
| *Artemisia tridentata* Nutt. (sagebrush) | − | − | − | − | − | − |
| *Cirsium arvense* L. (thistle) | − | − | − | − | − | − |
| *Euphorbla milii* Desmoul. (crown of thorns) | − | − | − | − | − | − |
| MONOCOTS | | | | | | |
| *Sorghum halapense* L. johnsongrass | − | − | − | − | − | − |
| *Poa annua* L. (annual bluegrass) | − | − | − | − | − | − |
| *Avena sativa* L. (park oat) | − | − | − | − | − | − |
| *Agropyrens repens* L. (quackgrass) | − | − | − | − | − | − |
| *Digitaria ischaemum* (Schreb) Muhl. (crabgrass) | − | − | − | − | − | − |
| *Zea mays* L. (corn) | − | − | − | − | − | − |

Compounds (2) and (3) (See Scheme above), cyclo(L-Pro-L-Phe) and cyclo(L-Pro-D-Phe), differ in phytotoxicity. The L, L diastereomer induces necrotic lesions on knapweed leaves at $10^{-4}$ M, but the L, D isomer is not active, even at $10^{-3}$ M Compounds (4), (5), (6) and (7) (See Scheme above) are not active toward knapweed at any of the test concentrations. These tests are repeated with hypocotyl tissue and similar results are obtained, and in 47% of these tests, cyclo(L-Pro-L-Tyr) induces lesions at $10^{-6}$ M.

In examining the diketopiperazines isolated and tested in this study it is apparent that certain functional groups are beneficial for activity. Maculosin, the most active isolate, possesses a phenolic moiety, not uncommon in phytotoxins (Sakamura, S. (1981) in Advances in Natural Products Chemistry, eds. Natori, A., Ikekawa, N. & Suzuki, M. (Halsted Press, New York) 91–105). The acidity of the hydroxyl proton may be instrumental in this activity.

It should be noted that this fungus also yields several other compounds phytotoxic to knapweed, including tenuazonic acid and certain perylenequinones, all of which possess fairly rigid skeletal conformations and reasonably acidic protons (Stierle, A. C., Cardellina, J. H., II & Strobel, G. A. (1987) J. Nat. Prod., submitted for publication).

The lesser activity of compound (2), cyclo(L-Pro-L-Phe) (See Scheme above), compared to the inactivity of its diastereomer, supports the importance of conformation to bioactivity, as well as the possible contribution of aromaticity.

Studies on diketopiperazines containing proline clearly delineate that L, L isolates assume an extended conformation that renders both the aromatic moiety and its hydroxyl group accessible (Young, P. E., Madison, V. & Blout, E. (1975) J. Am. Chem. Soc. 98, 5365–5371).

The yields of the various diketopiperazines are quite consistent in repeated fermentations. Maculosin is always the most abundant of the cyclodipeptides.

EXAMPLE 4

Selectivity and Specificity Tests

Maculosin had been established as a phytotoxin of spotted knapweed, but its selectivity or specificity must also be established. The test designed to establish the host-range of the toxin utilizes the simple leaf assay with a wide variety of plants.

Both monocots and dicots are included in the test range, among them several other composites. The assays are run at $10^{-3}$, $10^{-4}$, and $10^{-5}$ M. Maculosin consistently induces necrotic lesions on knapweed leaves but in no case is lesion induction observed on any other test plant.

The nineteen test plants are chosen somewhat at random, although an attempt is made to include several composites and plants known to be hosts to other form species of Alternaria alternata.

The results of this host-range challenge, while not exhaustive, clearly establish maculosin as the most host specific weed phytotoxin on record (see Table 2 hereabove for results).

Most studies on host specific phytotoxins have been focused on the effects of toxins on hybrid crop plants. Their extreme genetic similarity renders such hybrids susceptible to the onslaught of pathogenic fungi. Weeds are a genetically diverse lot and may actually vary from acre to acre in a well-established biome. History does not record the devastating loss of any major weed due to a microbial pathogen. A particular pathogen may decimate an isolated population of weeds while their neighbors are immune to the destruction. Throughout this study an attempt is made to use knapweed test plants grown from seeds from a variety of geographic locations to determine the limits of the activity of maculosin and other phototoxins. Some diversity is seen in the phytotoxicity results depending on the knapweed source.

Knapweed reproduces, in typical composite fashion, from wind-borne seeds carried from the parent plant. Seeds collected from plants within a twenty foot radius of the initial damaged specimen utilized in the example are the most affected by maculosin. Indeed, plants grown from seeds of this plant actually exhibited necrotic lesions when treated with $10^{-6}$ M maculosin in leaf assays.

Seeds were also collected from both Gallatin County and the Bitterroot Valley, Montana. Plants grown from these seeds were used to develop the assay results reported in Table 2. One plant was actually somewhat resistant to maculosin. Necrosis was only induced at $10^{-3}$ M.

The invention now being fully described, it will be apparent to one of ordinary skill in the art that many changes and modifications can be made thereto without departing from the spirit or scope of the invention as set forth herein.

I claim:

1. A method of selectively inducing chlorosis on a knapweed plant, comprising applying a knapweed phytotoxic amount of the 3,6-L,L isomer of a cyclodipeptide of the formula

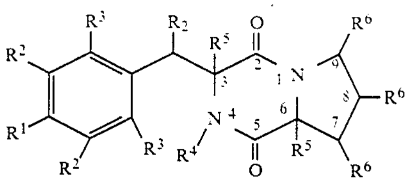

wherein $R^1$ is H and $R^2$ to $R^6$ are H, to the plant; and allowing for the cyclodipeptide to remain in contact with the plant for a period of time effective to attain said effect.

2. The method of claim 1, further comprising nicking the plant prior to applying the cyclodipeptide; and wherein the cyclodipeptide is applied to the nick to induce said chlorosis.

3. The method of claim 1, wherein the cyclodipeptide is applied to the unnicked plant to induce said chlorosis.

4. The method of claim 1, wherein the cyclodipeptide is in substantially pure form.

5. A method of selectively inducing chlorosis on a knapweed plant, comprising applying a knapweed phytotoxic amount of the 3,6 L,L isomer of a cyclodipeptide of the formula

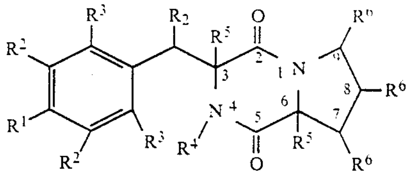

wherein $R^1$ is OH and $R^2$ to $R^6$ are H to the plant; and allowing for the cyclodipeptide to remain in contact with the plant for a period of time effective to attain said effect.

6. The method of claim 5, further comprising nicking the plant prior to applying the cyclodipeptide; and wherein the cyclodipeptide is applied to the nick to induce said chlorosis.

7. The method of claim 5, wherein the cyclodipeptide is applied to the unnicked plant to induce said chlorosis.

8. The method of claim 5, wherein the cyclodipeptide is in substantially pure form.

* * * * *